(12) United States Patent
French et al.

(10) Patent No.: US 7,492,457 B2
(45) Date of Patent: Feb. 17, 2009

(54) METHODS AND DEVICES FOR TESTING GERMICIDE ACTIVITY

(75) Inventors: Chris French, Mission Viejo, CA (US); Yvonne Tran, Murrieta, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 11/930,931

(22) Filed: Oct. 31, 2007

(65) Prior Publication Data

US 2008/0117422 A1 May 22, 2008

(51) Int. Cl.
*G01N 21/00* (2006.01)
(52) U.S. Cl. ...................... 356/436; 356/432
(58) Field of Classification Search ............... 356/432, 356/436
See application file for complete search history.

(56) References Cited

U.S. PATENT DOCUMENTS 5,853,952 A * 12/1998 Ushirogouchi et al. ... 430/270.1

* cited by examiner

*Primary Examiner*—Roy M Punnoose (57) ABSTRACT

A handheld device provides for measuring the concentration of dialdehyde in a dialdehyde solution. The device comprises (a) an optically transparent first container being under vacuum whereby to draw in a first predetermined quantity of the dialdehyde solution; (b) a first light source positioned to transmit light in the range of 420 nm to 620 nm through the optically transparent first container; (c) a first sensor positioned to receive the transmitted light, wherein the first sensor is configured to measure an optical absorbance of the transmitted light and configured to transmit an electronic signal proportional to the optical absorbance; and (d) a microprocessor in electronic communication with the first sensor, wherein the microprocessor is configured to indicate the concentration of the dialdehyde in the dialdehyde solution based on the electronic signal received from the first sensor.

16 Claims, 6 Drawing Sheets

Figure 6

METHODS AND DEVICES FOR TESTING GERMICIDE ACTIVITY

FIELD OF THE INVENTION

The invention relates to methods and devices for testing the activity of dialdehyde germicide compositions.

BACKGROUND OF THE INVENTION

It is essential that medical equipment that contacts semi-critical areas of the patient's body, such as mucous membranes or non-intact skin be clean and disinfected. Where the equipment is heat-sensitive, chemical disinfection or sterilization is required.

Dialdehydes, such as glutaraldehyde and ortho-phthalaldehyde, are known for their use in high-level disinfectant formulations for disinfecting medical equipment that contacts semi-critical areas of the patient's body. See, e.g., U.S. Pat. No. 4,851,449 (issued Jul. 25, 1989). Ortho-phthalaldehyde has broad-spectrum antimicrobial activity. Id.; U.S. Pat. No. 4,851,449. The FDA has cleared the ortho-phthalaldehyde disinfectant Cidex® OPA, which is now marketed commercially by Advanced Sterilization Products. Id. Cidex® OPA, comprises 0.55% ortho-phthalaldehyde, buffering agents, chelating agents and a corrosion inhibitor. See, Cidex® OPA Solution, 510(k) Summary of Safety and Effectiveness, K991487 (Oct. 6, 1999); see also, product literature at www.cidex.com. Other aromatic aldehydes also have antimicrobial activity, for example, U.S. Pat. No. 6,071,972, discloses disinfectant formulations comprising isophthalaldehyde or terephthalaldehyde, in a buffering system. And U.S. Pat. No. 5,223,166 (issued Jun. 29, 1993) discloses the use of disinfectant solutions comprising glutaraldehyde, glyoxal, malonaldehyde, and succinaldehyde.

Such dialdehyde compositions can be reused, but before such reuse, they must be tested to confirm that the minimum effective concentration of disinfectant is present. High quality and accuracy are desired. Further, equipment turn-around time is very important when considering methods for high-level disinfection and sterilization. Thus, test methods that determine disinfectant activity quickly are preferred.

In view of the foregoing, there is a need for devices and methods for fast, accurate determination of whether a minimum effective concentration of active ingredients is present in dialdehyde germicide compositions before reuse.

SUMMARY OF THE INVENTION

The invention provides methods and devices useful to assay dialdehyde germicide solutions to determine whether a minimum effective concentration of the dialdehyde is present. In certain embodiments, dialdehyde germicide solutions may optionally contain a carboxylate salt, such as potassium or sodium acetate, which increases the biocidal activity of the aldehyde germicide. Accordingly, in a preferred embodiment, methods and devices of the invention can determine whether a minimum effective concentration of the carboxylate salt is present. The germicide can be a disinfectant or sterilant In one embodiment, the invention provides a handheld device to confirm the activity of dialdehyde concentrations in germicide solutions, preferably, within 30-seconds. In a preferred embodiment, where the germicide solution comprises a carboxylate enhancer in addition to the dialdehyde, the hand-held device of the invention simultaneously or separately determines whether the carboxylate salt and dialdehyde are present in the minimum effective concentration.

In one embodiment, the fundamental measurement process is a highly selective reaction between an excess of a triazole compound and dialdehyde as a limiting reactant. In a preferred aspect of this embodiment, the dialdehyde is ortho-phthalaldehyde.

Dialdehyde germicide solutions, such as ortho-phthalaldehyde solutions, may optionally contain an organic carboxylate salt as an enhancing agent, for example, potassium or sodium acetate. Thus, in another embodiment, the invention provides a handheld device comprising a second analytical cell to determine whether a minimum effective concentration of carboxylate salt is present. In a preferred aspect of this embodiment, the concentration of the carboxylate salt is measured by optical absorbance of a pH indicator solution, for example, methyl orange, at 525-nm after reaction with dilute hydrochloric acid.

In preferred embodiments, the devices and methods of the invention offer substantially improved accuracy for reuse solutions over devices which use direct analysis with UV light, as UV analyzers cannot differentiate "active" ortho-phthalaldehyde from complexed (inactive) ortho-phthalaldehyde, and will suffer from interferences from other absorbers.

In preferred embodiments, vacuum ampoules with proper test reagents are used to sample the germicide solution. The amount of biocide sampled is carefully controlled by the level of vacuum, concentration and amount of reagent within each vacuum ampoule.

A handheld device according to the present invention provides for measuring the concentration of dialdehyde in a dialdehyde solution. The device comprises (a) an optically transparent first container being under vacuum whereby to draw in a first predetermined quantity of the dialdehyde solution; (b) a first light source positioned to transmit light in the range of 420 nm to 620 nm through the optically transparent first container; (c) a first sensor positioned to receive the transmitted light, wherein the first sensor is configured to measure an optical absorbance of the transmitted light and configured to transmit an electronic signal proportional to the optical absorbance; and (d) a microprocessor in electronic communication with the first sensor, wherein the microprocessor is configured to indicate the concentration of the dialdehyde in the dialdehyde solution based on the electronic signal received from the first sensor.

Preferably, the first container contains a reagent reactable with the dialdehyde to create a color change, such as a triazole, and more preferably 4-amino-3-hydrazino-5-mercapto-1,2,4-triazole.

An actuator is preferably connected to the first container and adapted for opening the container whereby to aspirate the predetermined quantity of dialdehyde solution into the container.

Preferably, the handheld device according further includes: an optically transparent second container being under vacuum whereby to draw in a second predetermined quantity of the dialdehyde solution; a second light source positioned to transmit light in the range of 420 nm to 620 nm through the optically transparent first container; and a sensor positioned to receive the transmitted light, wherein the sensor is configured to measure an optical absorbance of the transmitted light and configured to transmit an electronic signal proportional to the optical absorbance. Preferably, the second container contains a reagent reactable with a carboxylate within the dialdehyde solution, such as an acid in which case the second container also contains a pH indicator.

A method, according to the present invention, provides for measuring concentrations of a dialdehyde solution. The method comprises the steps of: (a) placing an optically transparent first vacuum ampoule into a handheld metering device; (b) aspirating a first predetermined quantity of the dialdehyde solution into the first vacuum ampoule; (c) passing light through the dialdehyde solution in the first ampoule and onto a first sensor in the handheld metering device; and (d) via a microprocessor electrically connected to the first sensor determining a concentration of dialdehyde in the dialdehyde solution based upon an output of the first sensor.

Preferably, the method further comprises the following steps: (e) placing an optically transparent second vacuum ampoule into the handheld metering device; (f) aspirating a second predetermined quantity of the dialdehyde solution into the second vacuum ampoule; (g) passing light through the dialdehyde solution in the second vacuum ampoule onto a second sensor in the handheld metering device which is electrically connected to the microprocessor; and (h) via the microprocessor determining a concentration of a carboxylate in the dialdehyde solution based upon an output of the second sensor.

Preferably, the results of steps (d) and (h) are displayed on the handheld device.

Other advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE FIGURES

These and other features, aspects, and advantages of the present invention will become better understood with regard to the following description, appended claims, and accompanying drawings where:

FIGS. 2A and 2B are top cross section of a device of the invention;

DETAILED DESCRIPTION

1. Devices and Methods of the Invention

A device of the invention comprises at least a test cell and an analytical component for measuring the concentration(s) of chemical species in the test cell.

In a preferred embodiment, a device of the invention comprises: (1) a test cell for containing a dialdehyde test solution; (2) a light source, preferably an LED for radiating light through the test cell; and (3) a sensor, with accompanying electronics for determining the optical absorbance of the contents within the test cell.

In a further embodiment, a device of the invention additionally comprises: (4) a test cell for containing a carboxylate test solution; (5) a light source, preferably an LED, for radiating light through the carboxylate test cell, and (6) a sensor, with accompanying electronics, for determining the optical absorbance of the contents within the carboxylate test cell.

In a more preferred embodiment, a device of the invention further comprises external pass fail indicators to alert the user whether the solution tested contains a minimum effective concentration of dialdehyde.

Upon addition of a dialdehyde germicide solution to the test cell of the device and mixing with the dialdehyde test solution, the dialdehyde quantitatively reacts with a dialdehyde analytical reagent present to give a reaction product. The dialdehyde test solution is chosen such that the dialdehyde reaction product's concentration is readily measurable by well-known analytical techniques, for example, by optical absorbance according to Beer's law. Once the concentration of the dialdehyde reaction product is known, the device analytically determines whether a minimum effective concentration of dialdehyde is present.

The carboxylate test cell may be included in a device of the invention when the dialdehyde germicide solution to be tested additionally contains an carboxylate salt enhancer, such as potassium or sodium acetate. Preferably, the carboxylate test cell contains an acidic carboxylate test solution containing a pre-selected, known concentration of acid. Upon addition of the germicide solution to the test cell and mixing with the carboxylate test solution, the carboxylate neutralizes the test solution's acid component. After such neutralization, pH analysis by the device of the invention indicates whether a minimum effective concentration of carboxylate salt is present in the germicide solution.

The test cells for dialdehyde and carboxylate concentrations can be two separated devices or integrated as one device. Therefore, the concentrations of dialdehyde and carboxylate in the test solution can be determined independently or simultaneously.

1.1 Definitions

As used herein, the term "germicide" means a disinfectant, high-level disinfectant, or sterilant. A "germicide" can be used to inactivate microorganisms with either a manual process or automated machine process.

As used herein, the term "minimum effective concentration" with respect to a dialdehyde germicide means the lowest concentration of dialdehyde necessary in the germicide, such that the germicide is effective for its intended biocidal use. One of skill in the art can readily select the minimum effective concentration based on the application for which the germicide is used. For example, in one embodiment, the minimum effective concentration of dialdehyde is the lowest dialdehyde concentration for which efficacy data are available to demonstrate that the biocide solution meets label claims.

As used herein, the term "minimum effective concentration" with respect to a carboxylate salt means the lowest concentration of carboxylate salt that must be present in the germicide such that the germicide is effective for its intended biocidal use. One of skill in the art can readily select a minimum effective concentration based on the application for which the germicide is used. For example, in one embodiment, the minimum effective concentration means the lowest carboxylate concentration for which efficacy data are available to demonstrate that the biocide solution meets label claims.

As used herein, the term "dialdehyde test solution" means a reagent containing a dialdehyde analytical reagent that reacts quantitatively with a dialdehyde germicide and wherein the concentration of the dialdehyde reaction product is readily measurable, for example, by absorbance using Beer's law.

As used herein, the term "carboxylate test solution" means a reagent comprising an acid, preferably a dilute strong inorganic acid, and a pH indicator. Preferably, the acid concentration in the test solution is pre-selected such that its complete neutralization represents that there is a minimum effective concentration of carboxylate salt in the germicide solution. Suitable inorganic acids include, but are not limited to, hydrochloric acid, sulfuric acid, phosphoric acid and nitric acid. Preferred pH indicators include, but are not limited to, methyl orange and ethyl orange.

As used herein, the term "dialdehyde analytical reagent", with respect to a dialdehyde germicide, means a chemical compound that when mixed with a dialdehyde germicide solution, quantitatively reacts with the dialdehyde to give a dialdehyde reaction product. Preferably the dialdehyde analytical reagent is 4-amino-3-hydrazino-5-mercapto-1,2,4-triazole.

As used herein, the term "dialdehyde reaction product" means a compound whose solution concentration is readily measurable by analytical techniques, preferably, by optical absorbance according to Beer's law. Preferably, the dialdehyde reaction product is the product of the reaction of the dialdehyde germicide with 4-amino-3-hydrazino-5-mercapto-1,2,4-triazole.

1.2 Device of the Invention

Figure 1:
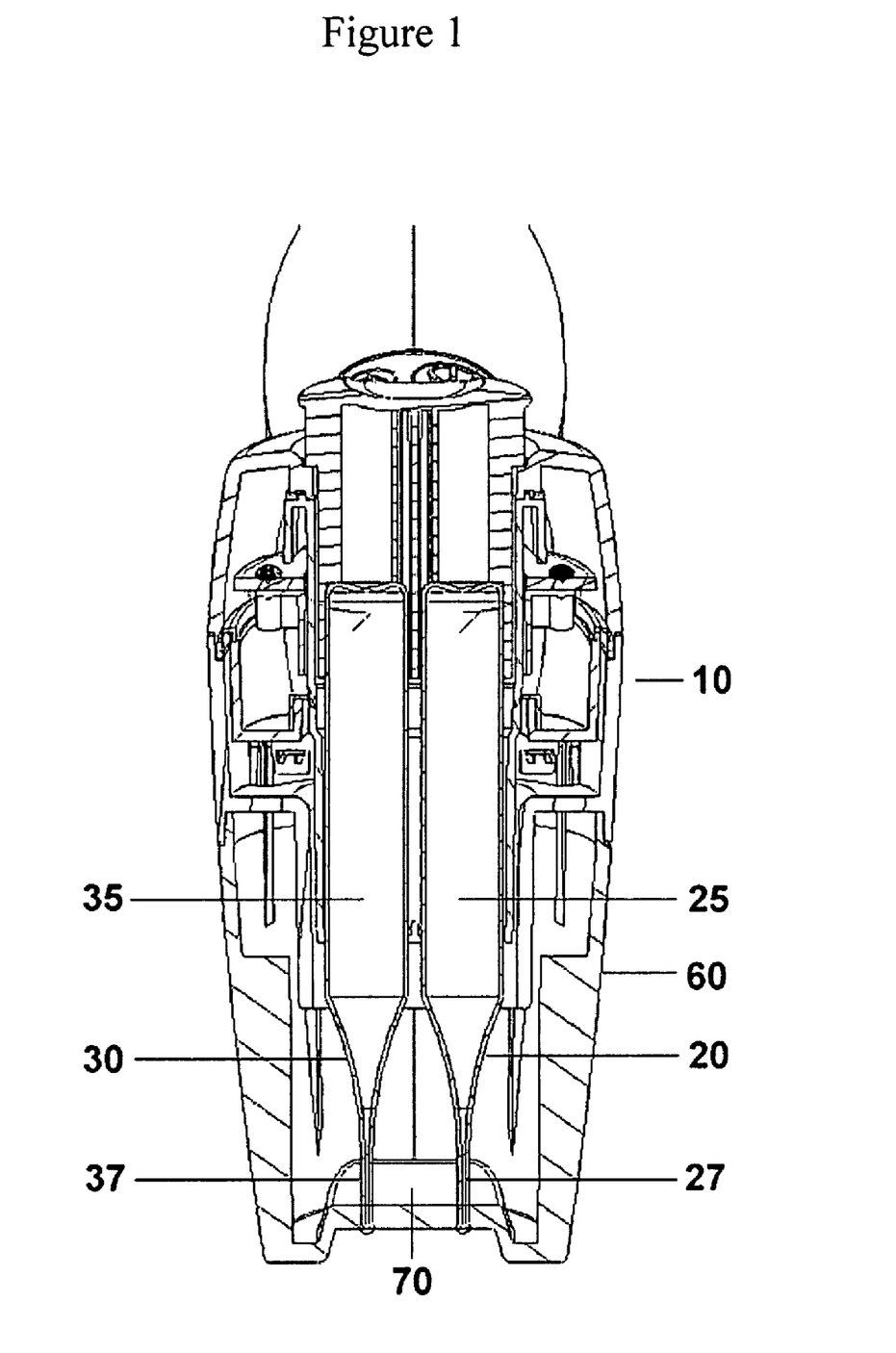
FIG. 1 is a front cross section of device of the invention.

FIG. 1 illustrates one embodiment of a device of the invention 10. Device 10 comprises test cell 20 for containing dialdehyde test solution 25. Device 10 optionally comprises test cell 30 for containing an organic carboxylate salt test solution 35. Test cell 30 is included in devices of the invention for testing the carboxylate concentration of dialdehyde germicide solutions that comprise an organic carboxylate salt enhancer. Test cells 20 and 30 comprise tips 27 and 37 respectively. In a preferred embodiment, test cells 20 and 30 are 2.5 ml polystyrene cuvettes or self-filling vacuum ampoules. Suitable cuvettes for use as test cells 20 and 30 are well known in the art.

Preferably, test cells 20 and 30 have a volume of from about 0.5 ml to about 7 ml. Preferably, test cells 20 and 30 are constructed of an optically transparent inert material, such as optically transparent polystyrene or glass. Device 10 comprises insertion head 60, wherein test cell tips 27 and 37 contact side wall 70 of insertion head 60.

Figure 2A:
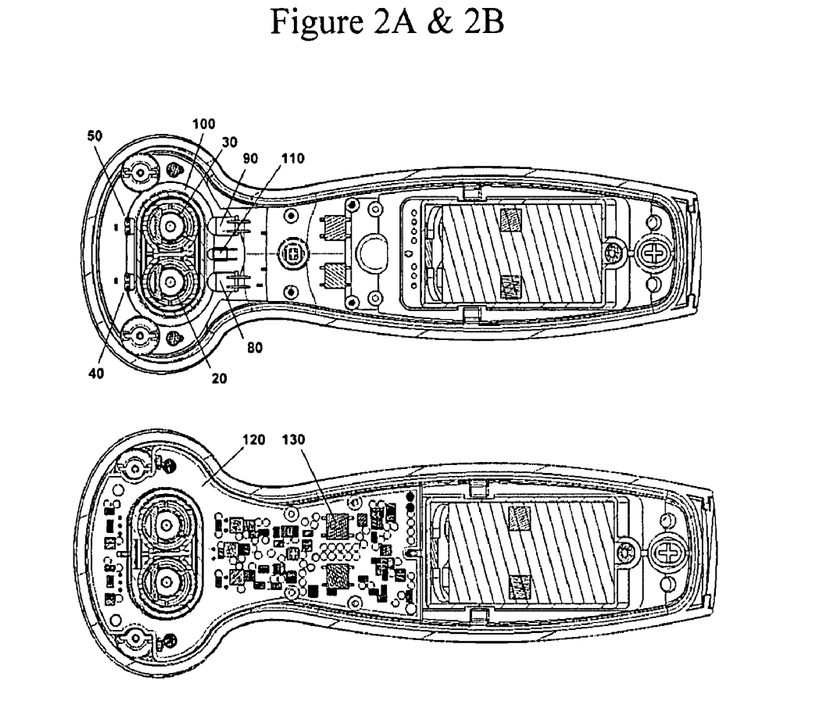
Figure 2C:
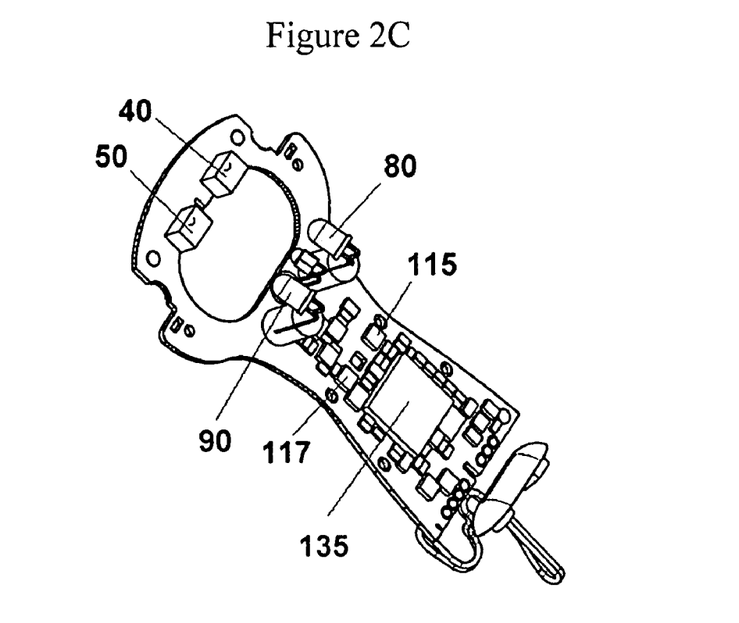
FIG. 2C is an underside of top cutaway view of a device of the invention
Figure 3:
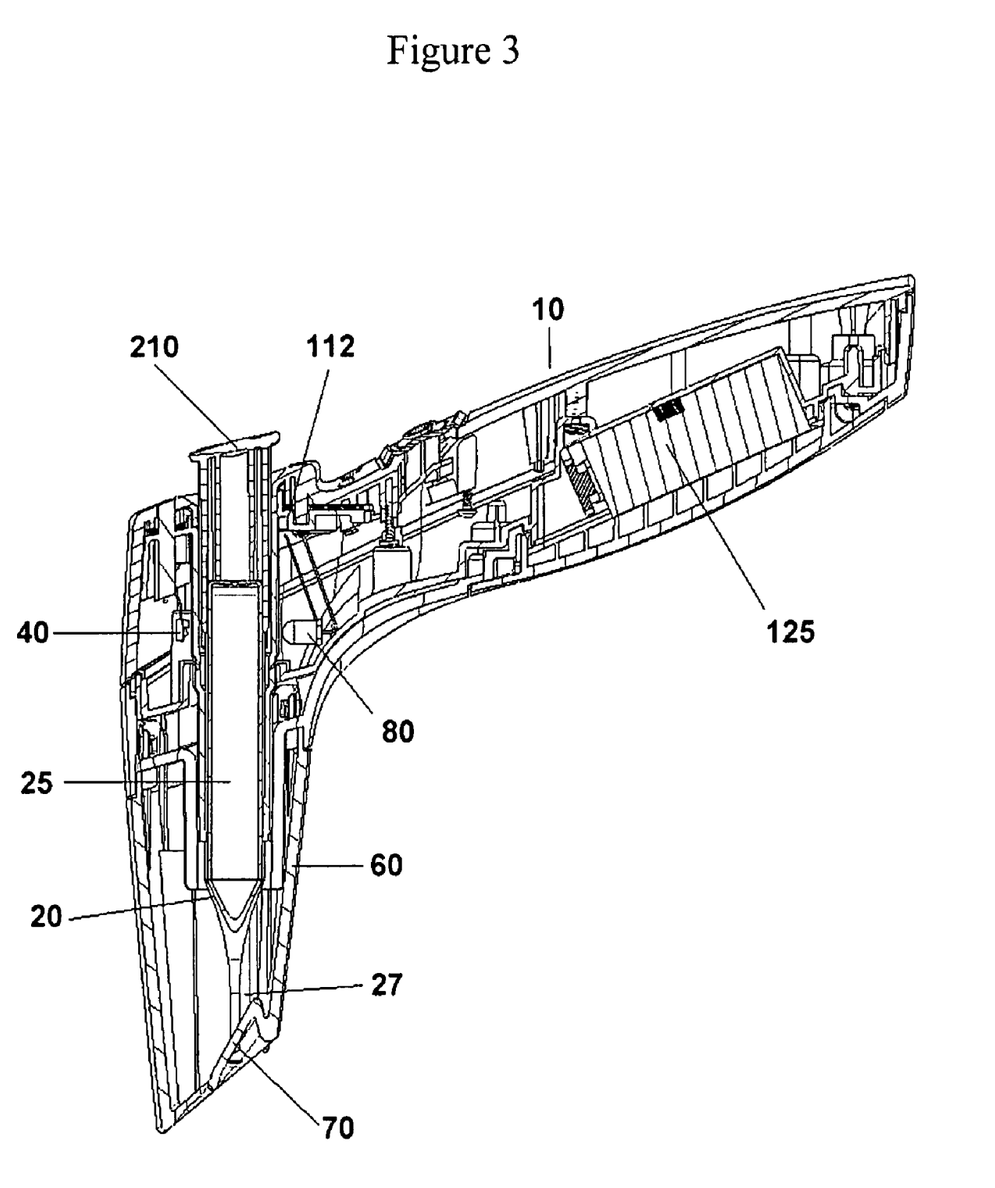
FIG. 3 is a side cross section of a device of the invention.

As shown in FIGS. 2A, 2B, and 2C sensors 40 and 50 are positioned orthogonal to analytical cells 20 and 30 such that each beam path generated by light sources 80 and 90 passes through the center of test cells 20 and 30 and impinges on their respective sensors 40 and 50 on the far side of cell 20 and 30. Such sensors or their equivalent are commercially available, for example, from Texas Advanced Optoelectronic Solutions.

Light sources 80 and 90 can be any light source that generates light at the appropriate wavelength with sufficient intensity. Additionally, if a broad-spectrum (white) LED or other type of light source is used, appropriate wavelengths may be selected by the use of colored filters that make the transmission of light selective. In this embodiment, dialdehyde test solution absorbance may be monitored between 350-nm and 800-nm, more preferably at 502-nm. Carboxylate test solution may be monitored with a white light source using a filter that transmits light with wavelengths higher than 500-nm.

According to sensors and methods well known in the art, light sensors 80 and 90 convert the light intensity to a proportional output voltage, which is monitored by a central microprocessor 135. Central microprocessors 135 for use in the invention are readily purchased or may be constructed according to well-known methods, and use of suitable central processors is well known by those of skill in the art. The electronic control system is based on microcontroller 135 which is readily commercially available, for example, from Freescale Semiconductor, Austin, Tex. An embodiment of the device of the invention may optionally utilize simple voltage comparator circuitry in place of a microprocessor.

Central microprocessor 135 then compares the voltage output with a stored calibration voltage, by well known methods at which time a "pass" or "fail" status may be assigned by microprocessor 135.

The frequency of the LED 80 is chosen such that it is absorbed by the dialdehyde reaction product formed by reaction between a dialdehyde analytical reagent and the dialdehyde germicide present in test solution 25. Preferably, LED 80 emits light at a frequency in the range of about 420 nm to about 620 nm, more preferably, at about 502 nm, which frequency is absorbed by the dialdehyde reaction product of ortho-phthalaldehyde and 4-amino-3-hydrazino-5-mercapto-1,2,4-triazole. The frequency of LED 90 is chosen such that it is absorbed by a pH indicator, for example, at a frequency of 525 nm which is absorbed strongly by methyl orange in the acid form, but less strongly in the base form.

Device 10 may comprise test cell 20 alone for containing dialdehyde test solution 25 without test cell 30. Device 10 may comprise test cell 30 alone for containing a organic carboxylate salt test solution 35 without test cell 20. Device 10 may comprise both test cells 20 and 30 for test both dialdehyde and carboxylate concentration simultaneously.

Test cell 30 is included in devices of the figures to illustrate the carboxylate concentration of dialdehyde germicide solutions that optionally comprise an organic carboxylate salt enhancer.

Test cells 20 and 30 comprise tips 27 and 37 respectively. In a preferred embodiment, test cells 20 and 30 are 2.5 ml polystyrene cuvettes or self-filling vacuum ampoules. Suitable cuvettes and/or self-filling vacuum ampoules for use as test cells 20 and 30 are well known in the art.

Preferably, test cells 20 and 30 have a volume of from about 0.5 ml to about 7 ml. Preferably, test cells 20 and 30 are constructed of an optically transparent inert material, such as optically transparent polystyrene or glass. Device 10 comprises insertion head 60, wherein test cell tips 27 and 37 contact side wall 70 of insertion head 60.

As shown in FIG. 2A, sensors 40 and 50 are positioned orthogonal to the analytical cells such that each beam path generated by LEDs 80 and 90 passes through the center of test cells 20 and 30 and impinges on their respective sensors 40 and 50 on the far side of cell 20 and 30.

As further shown in FIG. 2A, LEDs 80 and 90 are aligned with test cells 20 and 30 such that upon filling of tests cells 20 and 30 with test solution, for example actuation of self-filling vacuum ampoules, light from LEDs 80 and 90 passes through the center of test cells 20 and 30. According to sensors and methods well known in the art, light sensors 40 and 50 convert the light intensity to a proportional output voltage, which is monitored by a central microprocessor 135. Central processor 135 for use in the invention are readily purchased or may be constructed according to well-known methods, and use of suitable central processors is well known by those of skill in the art.

Central microprocessor 135 then compares the voltage output with a stored calibration voltage, by well known methods at which time a "pass" or "fail" status may be assigned by microprocessor 135.

The frequency of the LED 80 is chosen such that it is absorbed by the dialdehyde reaction product formed by reaction between a dialdehyde analytical reagent and the dialdehyde germicide present in test solution 25. Preferably, LED 80 emits light at a frequency in the range of about 420 nm to about 620 nm, more preferably, at about 502 nm, which frequency is absorbed by the dialdehyde reaction product of ortho-phthalaldehyde and 4-amino-3-hydrazino-5-mercapto-1,2,4-triazole. The frequency of LED 90 is chosen such that it is absorbed by a pH indicator, for example, at a frequency of 525 nm which is absorbed strongly by methyl orange in the acid form, but less strongly in the base form.

Device 10 further comprises sample compartment 100 for receiving test cell 20 and optional test cell 30. Test cell 20 and optional test cell 30 are integrated within a test cell holder that maintains the optimum position of the test cell within reader 10. The test cell and test-cell holder assembly may be inserted into the top of sample compartment 100 until the first physical stop is reached. The first physical stop may be affected with the use of spring-loaded plunger 112 that prevents premature actuation of test solutions 25 and/or 35. At which time the tip(s) 27 and or 37 are submerged into the dialdehyde biocide solution to be tested, the user may choose to actuate test solutions 25 and/or 35 by pushing gently on the rear face 210 of tests cells 20 and/or 30 to the second physical stop. A third LED 110 may optionally be used to monitor the position of tests cells 20 and/or 30 and may be used to actuate the software that controls the analysis. Such software that controls the analysis is well known in the art.

Upper portion 120 of device 10 comprises internal electronics 130. The electronic control system is based on microcontroller 135 which is readily commercially available, for example, from Freescale Semiconductor, Austin, Tex.

Microcontroller 135 may be used to execute well known software that recognizes the actuation of test solutions 25 and/or 35, provides a time delay for reaction and mixing with an active component and interprets the output from the light to voltage transformers 40 & 50. Microcontroller 135 may optionally use electronically erasable programmable read-only memory (EEPROM) to store reference or calibration voltages. erasable programmable read-only memory (EEPROM) is commercially available, for example, from ST Microelectronics.

Figure 4:
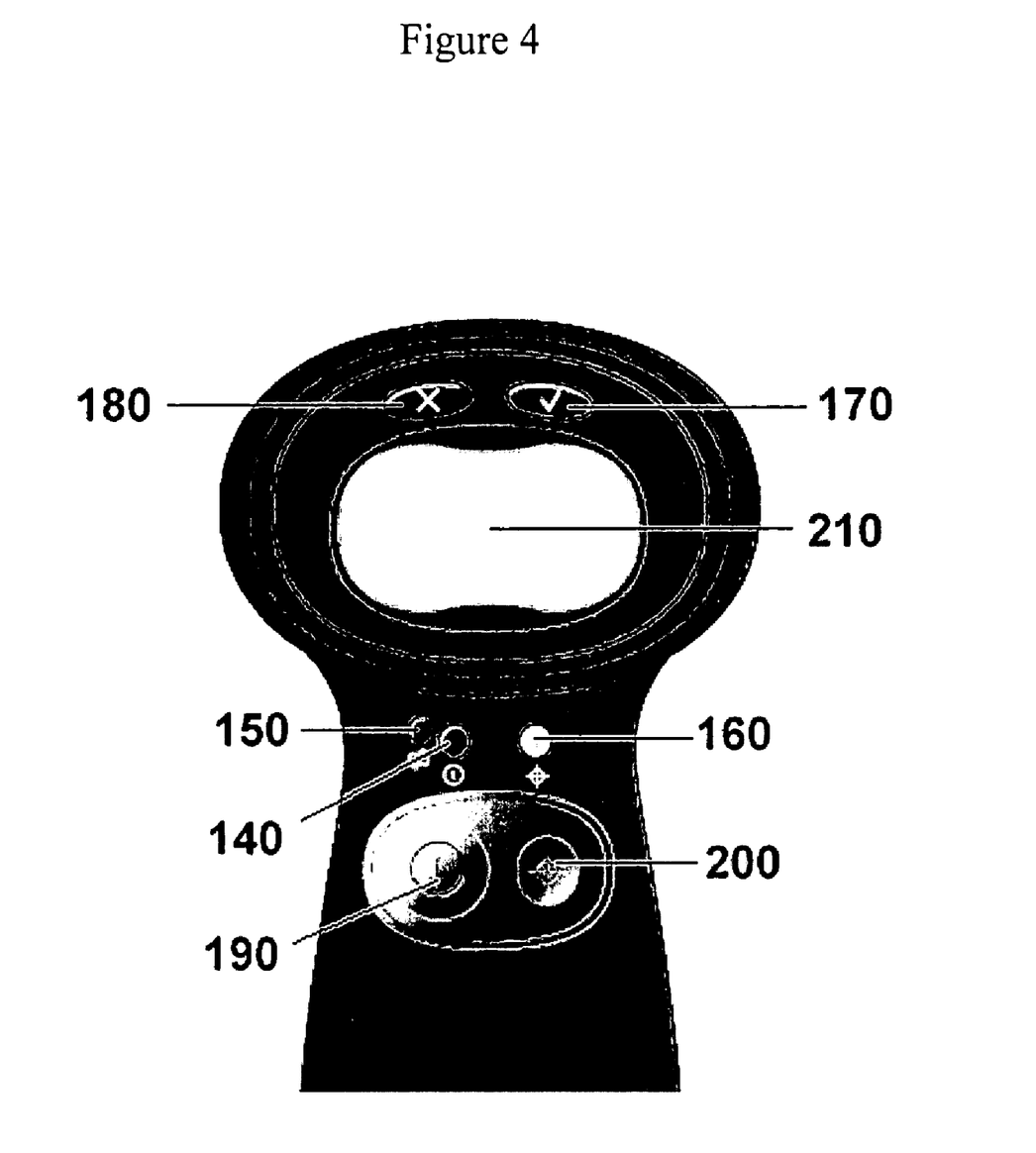
FIG. 4 is an image of the user interface design.
Figure 5:
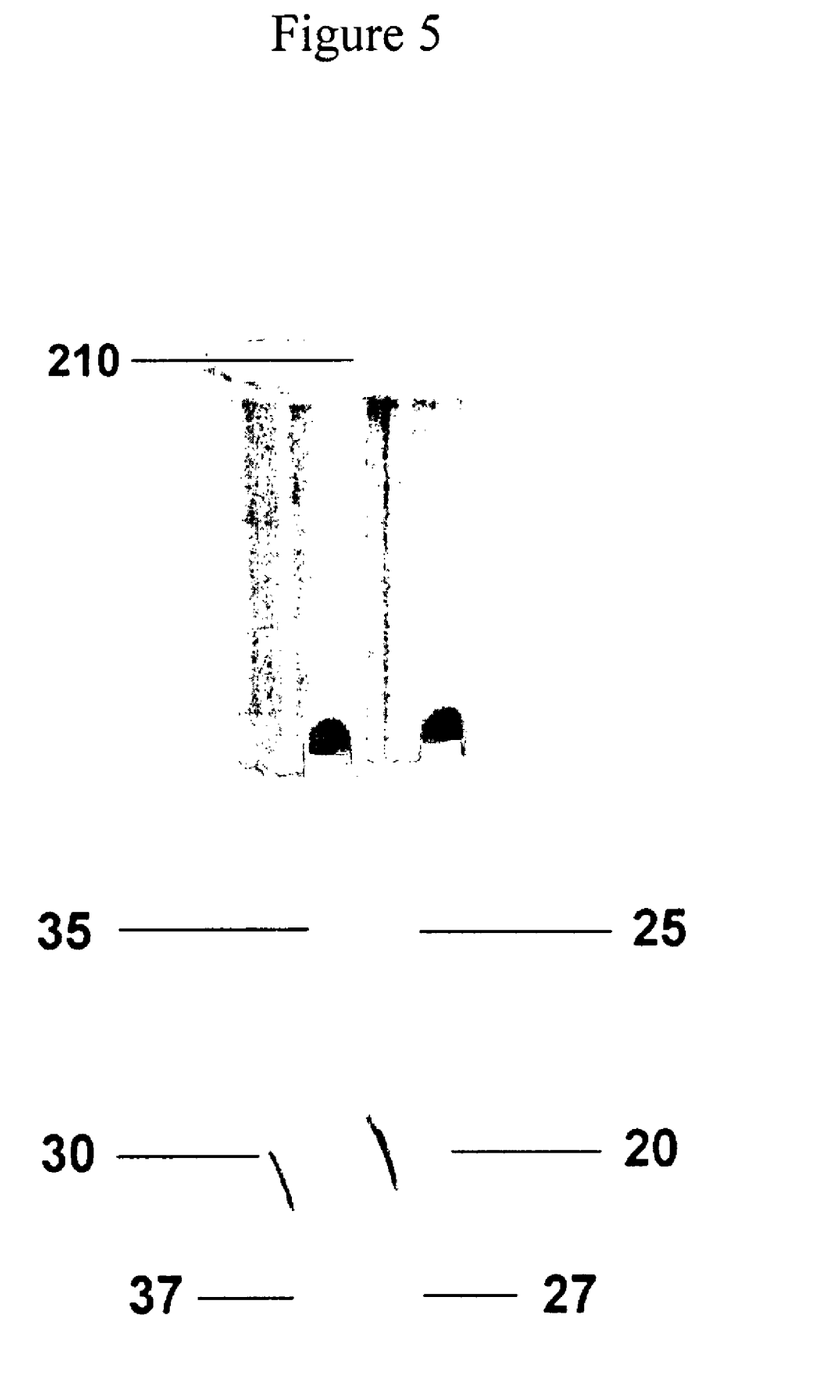
FIG. 5 is an image of integrated, self filling vacuum analytical cells.

Microcontroller unit 135 may also recognize user input through external button 190 (as shown in FIG. 4) that may be used to turn power on or off, or to perform a calibration process. Power from a single 9 volt battery 125 may be managed by a voltage regulators 115 & 117, commercially available, for example from National Semiconductor. Power from such regulators 115 & 117 may be used to provide stable current supplies to high-intensity LEDs 80 and 90, such as those provided by Everlight Electronic Company.

Light intensity on the far side of analytical cells 20 and/or 30 can be measured independently by light to voltage transformers 40 & 50, which are commercially available, for example, from Texas Advanced Optoelectronic Solutions. Optionally, Bluetooth® electronics may transmit pass/fail indications to a remote printer or computer interface.

Outer shell of device 10 further comprises five user interface indicators 140, 150, 160, 170 and 180. The user interface is designed to indicate the status of both the device and the results of the biocide tests. Indicator 140, a round, green LED, illuminates when the user depresses the power key 190 to indicate that power is on. Conversely, when the user depresses the power key for more than three seconds, indicator 140 will cease to illuminate indicating that power is no longer applied. Indicator 150, a round, red LED, illuminates when the battery no longer is capable of supplying sufficient voltage to properly execute the analysis. Indicator 160, a round, orange LED, illuminates when the user depresses the "calibrate" button 200.

Device 10 further comprises a signal component 170, preferably an external LED, more preferably a green LED, which activates when the concentrations of dialdehyde and/or carboxylate are found to be above the minimum effective concentrations, thereby alerting the user that the germicide solution can be used. If the germicide solution does not have a minimum effective concentration of active ingredients, signal component 180, preferably an LED, more preferably a red LED, activates notifying the user that the solution is not suitable for use. If an error is noted before or during the analysis, all LEDs will flash together and a test is not permitted.

The device may be activated by way of monitoring a third LED 110, the light from which is blocked from the sensors opposite the analytical cells upon actuation. Device 10 further comprises actuator button 210, which when depressed by the user, physically compresses tips 27 and 37 against wall 70. The germicide solution to be tested then aspirates into test cells 20 and 30 simultaneously and mixes with the aldehyde test solution 25 and the carboxylate test solution 35 respectively. Sample is aspirated into analytical cells 20 and/or 30 due to the vacuum under which the cells are manufactured. The amount of biocide sampled is carefully controlled by the amount of reagent within each vacuum ampoule, as the sample will fill the remaining volume of evacuated cells 20 and/or 30.

In a preferred embodiment, by way of the device of the invention, the device may be calibrated by using cells 20 and/or 30 filled with calibration solutions. Calibration solutions may assume the same packaging configuration as dialdehyde test solution and carboxylate test solution, however will be limited in length such that tips 27 and 37 do not contact side wall 70 when actuated. The user may optionally insert the calibration solutions into a device of the invention, and depress a calibration button 200 at which time indicator 160 may illuminate. Actuating the calibration cells causes the electronics to pass light through both cells as described above, with the exception that voltage output from the light-to-voltage transformers are not used to make a pass/fail decision but are rather stored in the EEPROM and are used as reference voltages in subsequent analyses.

Alternatively, an embodiment of a device of the invention may use both cells 20 and 30 to measure only one active ingredient of a biocide solution. In this embodiment, both test cells 20 and 30 may contain either dialdehyde test solution or both cells 20 and 30 may optionally contain carboxylate test solution. In this embodiment the LEDs selected for both cells would be either 502-nm for dialdehyde test solution or 525-nm for carboxylate test solution. Using both cells to perform parallel tests will permit the performance of duplicate tests for the same solution with one averaged result reported to the end user for greater confidence.

Optionally, two cells may be used to measure a single active ingredient in a biocide solution using one cell as a "background reference." In this embodiment, one cell of the pair (e.g., 20) may optionally contain either dialdehyde test solution or carboxylate test solution. The other cell (e.g., 30) would be held under vacuum and may contain water or no test solution to provide a sample of the biocide's natural coloration. In this embodiment, according to well known methods, the absorbance at the appropriate wavelength of the background solution may be subtracted from the absorbance of the test solution after the reaction time has elapsed to provide a correction for background coloration. This test system may be useful if a biocide solution under test is badly discolored by interfering materials.

Alternatively, an embodiment of a device of the invention may use only one of the two cells for a given test to measure only one active ingredient of a biocide solution. In this embodiment, the user will place only a dialdehyde test ampoule 20 into the sample compartment 100 for measurement of dialdehyde concentration. The user may also choose to place only a carboxylate test ampoule 30 into the sample compartment 100 for measurement of carboxylate concentration. For single active testing the user would select the appropriate test selection switch to ensure the microprocessor reads only the ampoule under test.

Figure 6:
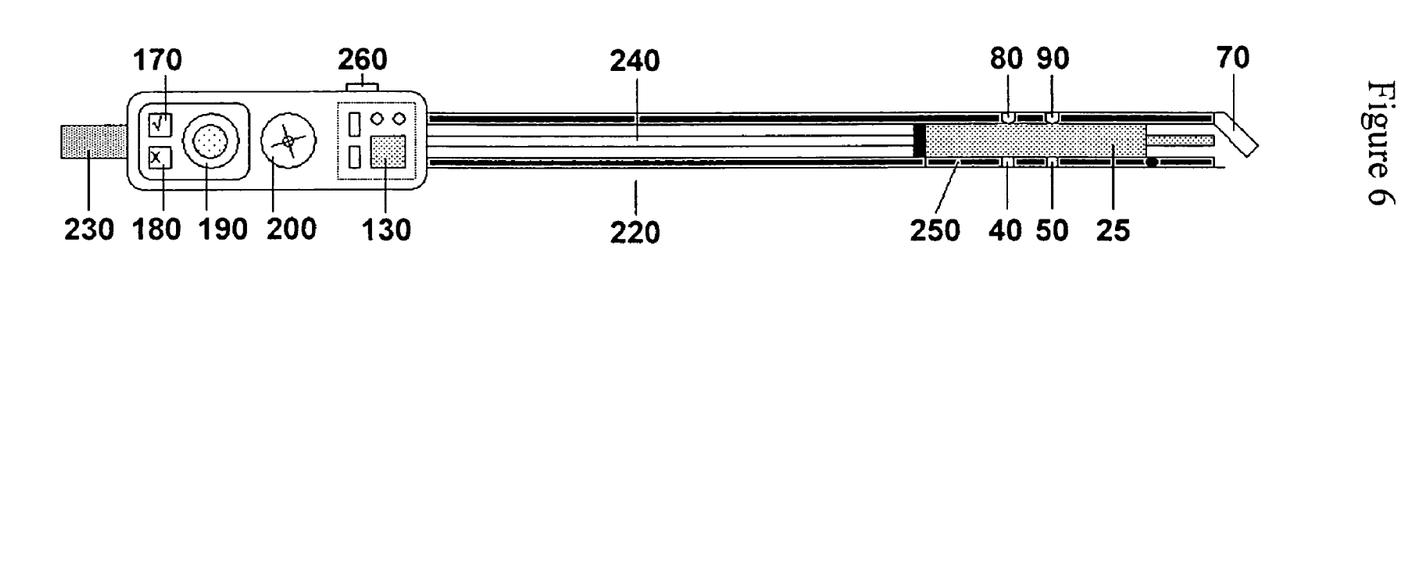
FIG. 6 is a device of the invention for use with single reagent tests.

FIG. 6 illustrates another embodiment of a device of the invention 220. In this embodiment, a single test solution is used to test only one chemical component of a biocide using a "wand" shaped device for easy sampling through small sampling ports. With the design exhibited in FIG. 6, a user may place either a dialdehyde or carboxylate test solution ampoule 25 into the tip of the monitor using a hinged sample compartment 250. The user may depress power button 190, and actuation button 230 to initiate the sampling and analysis of the biocide solution.

As discussed above, an LED 80 or 90 creates transmits light through test solution 25 and the light intensity after passing through the solution is measured by light to voltage converter 40 or 50. The monitoring electronics 130 are attached via a ribbon cable to devices 40, 50, 80 and 90 to provide power and to monitor output voltage of device 40 or 50. Plastic bar 240 transmits pressure from actuation button 230 to the test ampoule which is actuated by applying pressure against wall 70. After the test is completed, LED 170 or 180 will illuminate to indicate passing or failing results, respectively. Aldehyde test solution may be monitored between 350-nm and 800-nm or with a "white" LED 80, or more preferably a 502-nm LED. Carboxylate test solution may be monitored between 450 and 650-nm, more preferably with a 525-nm LED 90. As well, a single LED in the range of 450 and 650-nm, more preferably a 525-nm LED, will suffice for measuring both dialdehyde test solution or carboxylate test solution.

An embodiment of a device of the invention may be calibrated using sealed ampoules filled with calibration solution as previously described. In this embodiment, the user may optionally press button 200 to change the device 220 to "calibrate" mode. Actuation of the calibration consumable initiates a routine to measure the absorbance of the solution by probing the voltage output of devices 40 and/or 50. Such reference voltages may be stored in the EEPROM of the device and used to make pass/fail determinations for subsequent tests.

Alternatively, the "single-cell" embodiment of the device may incorporate two LEDs with a user-selectable wavelength. Multiple wavelengths for various reagents may be readily achievable by incorporating multiple LEDs within the body of the device. Power will be supplied to the appropriate LED and light to voltage converter based on the user's selection of the appropriate test using selector switch 260. Selecting the test for dialdehyde solution activates only the internal 502-nm LED, while selecting the test for carboxylate solution activates only a 525-nm LED. The pass/fail indication would pertain only to the active ingredient under the selected test.

Additionally, by way of the device of the invention, user selection switch 260 may be eliminated in favor of automatic recognition of the test type by features of the device. In this embodiment, the consumable may be shaped in such a fashion that the shape of the device actuates "key" switches within sample door 250, thereby indicating to the microprocessor the correct LED (80 or 90) and sensor (40 or 50) to activate to perform the analysis. In an alternative embodiment, following the closure of door 250, LED 80 or 90 may activate to determine which test is appropriate based on the pre-actuation absorbance of the consumable. In this embodiment, the pre-actuation absorbance of the dialdehyde test solution may be differentiated from the pre-actuation absorbance of the carboxylate test solution, as the latter test reagent is colored while the former is not. In this way, the device may optionally determine the identity of the test by pre-actuation color, then apply the appropriate test based on this determination without the need for physical difference in ampoule shape.

1.3 The Dialdehyde Test Solution

The composition of the dialdehyde test solution comprises a dialdehyde analytical reagent. The dialdehyde analytical reagent is selected by those of skill in the art such that it quantitatively and irreversibly reacts with the particular dialdehyde germicide being used to produce a dialdehyde reaction product. The concentration of the dialdehyde reaction product is measured by the analytical components of the device of the invention. Once the concentration of the dialdehyde reaction product is determined, the concentration of the dialdehyde in the germicide solution is readily calculated.

Preferably, such a reaction is quantitatively complete within from about 1 second to about 60 seconds, more preferably, of from about 5 seconds to about 25 seconds. After such reaction, analysis of one or more properties of the resulting mixture by way of the device of the invention indicates whether the minimum effective concentration of dialdehyde is present in the dialdehyde germicide solution.

In a preferred embodiment, the dialdehyde test solution comprises a molar excess of a dialdehyde analytical reagent, wherein the concentration of the dialdehyde reaction product is measured by optical absorbance according to Beer's law. In this embodiment, the device of the invention measures the concentration of the dialdehyde by measurement of optical absorbance, at a suitable wavelength, of the dialdehyde reaction product resulting from treating the dialdehyde test solution with the dialdehyde germicide solution. Voltage output from a light sensor opposite a blue-green LED must reach a point less than a calibrated set point due to the absorbance of light by the reaction complex.

In one embodiment, the dialdehyde test solution is chosen such that the dialdehyde analytical reagent reacts with the dialdehyde to form an intensely colored complex. Preferably, the color intensity of the reaction mixture stabilizes in about 1 second to about 2 minutes, more preferably, about 5 to about 20 seconds. The absorbance of the complex in the solution using excess dialdehyde analytical reagent and dialdehyde as the limiting reactant is proportional to the concentration of the dialdehyde in the solution by Beer's Law.

Examples of preferred dialdehyde analytical reagents useful in the present invention include, but are not limited to, 4-amino-3-hydrazino-5-mercapto-1,2,4-triazole and a sodium sulfite/phenolphthalein composition.

EXAMPLE

Dialdehyde Test Solution Composition 1

| chemical | wt. % |
| --- | --- |
| 4-amino-3-hydrazino-5-mercapto-1,2,4-triazole | 4% |
| Solution of KOH | 0.81% |
| Balance water | — |

Alternatively, a dialdehyde test solution may contain sodium sulfite which on reaction with ortho-phthalaldehyde forms hydroxide ion that induces a pH shift and subsequent change in color of the dialdehyde test solution. The complete neutralization of a known concentration of acid that is also present in the test solution, for example, but not limited to L-glutamic acid, represents the presence of at least the minimum effective concentration of ortho-phthalaldehyde. Biocide solutions with ortho-phthalaldehyde concentrations in excess of the minimum effective concentration neutralize the contained acid and cause the solution to become basic. The pH shift causes color changes in pH indicators, including but not limited to phenolphthalein and bromocresol green.

EXAMPLE

Dialdehyde Test Solution Composition 2

| chemical | wt. % |
| --- | --- |
| sodium sulfite | 3% |
| ethanol | 10% |
| phenolphthalein | 0.1% |
| L-glutamic acid | 0.11% |
| bromocresol green | 0.006% |
| balance water | |

The above test solutions are prepared by mixing the reagents together at room temperature. Up to 400 g/L alkali halide salt, preferably 200 g/L potassium chloride, may be added to increase the density of the mixture to improve automatic mixing.

Test solution composition two may alternatively be used with glutaraldehyde, glyoxal, malonaldehyde, and succinaldehyde-based germicide solutions, with minor modifications to sodium sulfite and L-glutamic acid concentrations to accommodate a wide variety of products with different specifications for minimum effective concentration.

1.4 The Carboxylate Salt Test Solution

The composition of the test solution for measuring carboxylate concentration is selected by one of skill in the art such that when it mixes with the subject dialdehyde/carboxylate germicide solution, a component of the test cell solution neutralizes the carboxylate salt. After such reaction, analysis of component concentrations or one or more properties of the resulting solution by the device of the invention indicates whether a minimum effective concentration of carboxylate salt is present in the germicide solution.

In a preferred embodiment, the carboxylate test solutions for use in the device of the invention comprises an acid, preferably a dilute, strong inorganic acid, and a pH indicator. The acid concentration in the test solution is pre-selected such that its complete neutralization represents that there is a minimum effective concentration of carboxylate salt in the germicide solution. Suitable inorganic acids include, but are not limited to, hydrochloric acid, sulfuric acid, phosphoric acid and nitric acid. Suitable pH indicators include, but are not limited to, methyl orange or ethyl orange.

In a preferred embodiment, by way of the device of the invention, a known volume of the dialdehyde/carboxylate salt germicide solution is treated with the inorganic acid test solution comprising a pH indicator. If a minimum effective concentration of the carboxylate salt is present, the inorganic acid will have been completely neutralized, thereby increasing the pH of the test solution. The device of the invention determines complete neutralization by the optical absorbance of the pH indicator.

EXAMPLE

Carboxylate Test Solution Composition 1

| chemical | Range wt. % |
| --- | --- |
| hydrochloric acid solution | 4.625% |
| methyl orange | 216 ppm |
| Ethylene glycol | 35% |
| Balance water | — |

1.5 The Calibration Solutions

Calibration solutions are fashioned from dye solutions, preferably FD&C or D&C dye solutions, or more preferably from solutions of FD&C #40 or FD&C #4. The dye solutions are intended to very nearly approximate the solution absorbance of carboxylate or dialdehyde test solution(s) after reacting with biocide solutions with active ingredients just in excess of their minimum effective concentration(s). In a preferred embodiment, by way of the device of the invention, the user may calibrate the device to ensure drift in electronics or optics does not affect the accuracy of the experiment by adjusting the setpoint voltages used to make pass/fail decisions. Calibration devices are filled nearly completely, sealed, and do not need to aspirate biocide solution.

Optionally, the calibration solutions may contain 50% 1,2-propanediol to prevent freezing during shipment in cold climates.

Example Calibration Solution

| chemical | Range wt. % |
| --- | --- |
| FD&C Red #40 | 100-300 ppm |
| 1,2-propanediol | 35% |
| balance water | |

2. Methods of the Invention

The methods of the invention are useful to assay dialdehyde germicide solutions to determine whether a minimum effective concentration of the dialdehyde is present. In certain embodiments, dialdehyde germicide solutions may optionally contain a carboxylate salt, such as potassium or sodium acetate, which increases the biocidal activity of the aldehyde germicide. In one embodiment, devices of the invention are useful to determine whether a minimum effective concentration of the carboxylate salt is present.

The minimum effective concentration of dialdehyde and carboxylate salt (if included) depend on the application for which the biocide solution is to be used. One of skill in the art will readily pre-select a specific minimum effective concentration depending on a number of factors. Table 1 sets forth some guidelines regarding the minimum effective concentration of ortho-phthalaldehyde in an aqueous solution. Table 2 sets forth guidelines regarding the minimum effective concentration of potassium acetate when used in a 0.55 wt % ortho-phthalaldehyde solution.

TABLE 1

Minimum Effective Concentration of ortho-Phthalaldehyde

| Application | Minimum Effective Concentration of ortho-phthalaldehyde |
|---|---|
| Disinfecting Endoscopes | 0.3 wt % |

TABLE 2

Minimum Effective Concentration of Potassium Acetate in an 0.55% Ortho-Phthalaldehyde Solution

| Application | Minimum Effective Concentration of Potassium Acetate |
|---|---|
| Disinfecting Endoscopes | 5.0% |
| Sterilizing surgical equipment | 5.0% |

In use, test cell 20 may be loaded by pipette with dialdehyde test solution 25, for example, 3.15 mL of dialdehyde test solution 25 set forth in the Table 3 below. Test cell 20 may alternatively be pre-packaged to contain 3.15 mL of dialdehyde test solution 25 within self-filling, vacuum ampoules. Test cell 30 may be loaded by pipette with carboxylate test solution 35, for example, 2.26 mL of acetate test solution 30, whose composition is set forth in Table 4 below. Test cell 30 may alternatively be pre-packaged to contain 2.26 mL of acetate test solution 35 within self-filling, vacuum ampoules.

TABLE 3

Dialdehyde Test Solution Composition 25a

| chemical | wt. % |
|---|---|
| 4-amino-3-hydrazino-5-mercapto-1,2,4-triazole | 4% |
| solution KOH | 0.81% |
| Balance water | |

TABLE 4

Carboxylate Test Solution Composition 30a

| chemical | wt. % |
|---|---|
| hydrochloric acid solution | 4.625% |
| methyl orange | 216 ppm |
| Ethyl glycol | 35% |
| Balance water | |

The test solutions are prepared by mixing the reagents together at room temperature.

Referring to Figures, test cells 20 and 30 are inserted through compartment 100, wherein the test cell tips enter insertion head 60, which tips contact side walls 70. Power switch 190 is activated. Insertion head 60 is dipped into the germicide solution to be tested. The user depresses actuator button 210, which physically compresses tips 27 and 37 against wall 70. Bending the tips opens the consumable and allows the solution to fill the vacuum within the consumable's analytical cells. The germicide solution to be tested then aspirates into test cells 20 and 30 simultaneously and mixes with the aldehyde test solution 25 and the carboxylate test solution 35 respectively.

The LEDs 80 and 90 emit light through the test cells 20 and 30 and into sensors 40 and 50 respectively. The dialdehyde test solution 25 comprises a molar excess of a dialdehyde analytical reagent, wherein the concentration of the dialdehyde reaction product is measured by optical absorbance according to Beer's law. In this embodiment, the device of the invention measures the concentration of the dialdehyde by measurement of optical absorbance, at a suitable wavelength, of the mixture resulting from treating the dialdehyde test solution with the dialdehyde germicide solution.

In a preferred embodiment, the dialdehyde analytical reagent of test solution 25 is 4-amino-3-hydrazino-5-mercapto-1,2,4-triazole, which quantitatively reacts with ortho-phthalaldehyde to give a reaction product that absorbs at 502 nm. Voltage output from a light sensor 40 opposite a blue-green LED 80 must reach a point less than a calibrated set-point due to the absorbance of light by the reaction complex.

Test solution 35 is used to measure the concentration of the carboxylate salt by optical absorbance of a pH indicator solution at an appropriate wavelength. Test solution 35 comprises an organic acid, such as hydrochloric acid and a pH indicator such a methyl orange, in which case LED 90 operates at 525 nm. Voltage output from light sensor 50 must be greater than a calibrated set point indicating HCl was titrated with excess, remaining carboxylate salt allowing the indicator to change from red to an orange color.

If the concentrations of dialdehyde and carboxylate are found to be above the minimum effective concentrations, signal component 170 activates. If either the dialdehyde or the carboxylate salt is not present in a minimum effective concentration, signal component 180 activates. After testing, the user discards the test solutions in waste box and rinses the tip of device 10 to remove any residual germicide solution.

What is claimed is:

1. A handheld device for measuring the concentration of dialdehyde in a dialdehyde solution comprising:
   (a) an optically transparent first container being under vacuum whereby to draw in a first predetermined quantity of the dialdehyde solution;
   (b) a first light source positioned to transmit light in the range of 420 nm to 620 nm through the optically transparent first container;
   (c) a first sensor positioned to receive the transmitted light, wherein the first sensor is configured to measure an optical absorbance of the transmitted light and configured to transmit an electronic signal proportional to the optical absorbance; and
   (d) a microprocessor in electronic communication with the first sensor, wherein the microprocessor is configured to indicate the concentration of the dialdehyde in the dialdehyde solution based on the electronic signal received from the first sensor.

2. A handheld device according to claim 1 wherein the first container contains a reagent reactable with the dialdehyde to create a color change.

3. A handheld device according to claim 2 wherein the reagent comprises a triazole.

4. A handheld device according to claim 3 wherein the triazole comprises 4-amino-3-hydrazino-5-mercapto-1,2,4-triazole.

5. A handheld device according to claim 1 and further comprising an actuator connected to the first container for opening the container whereby to aspirate the predetermined quantity of dialdehyde solution into the container.

6. A handheld device according to claim 1 and further comprising:
- an optically transparent second container being under vacuum whereby to draw in a second predetermined quantity of the dialdehyde solution;
- a second light source positioned to transmit light in the range of 420 nm to 620 nm through the optically transparent first container; and
- a sensor positioned to receive the transmitted light, wherein the sensor is configured to measure an optical absorbance of the transmitted light and configured to transmit an electronic signal proportional to the optical absorbance.

7. A handheld device according to claim 6 wherein the second container contains a reagent reactable with a carboxylate within the dialdehyde solution.

8. A handheld device according to claim 7 wherein the reagent comprises an acid and the second container also contains a pH indicator.

9. A method for measuring concentrations of a dialdehyde solution, the method comprising the steps of:
- (a) placing an optically transparent first vacuum ampoule into a handheld metering device;
- (b) aspirating a first predetermined quantity of the dialdehyde solution into the first vacuum ampoule;
- (c) passing light through the dialdehyde solution in the first ampoule and onto a first sensor in the handheld metering device; and
- (d) via a microprocessor electrically connected to the first sensor determining a concentration of dialdehyde in the dialdehyde solution based upon an output of the first sensor.

10. A method according to claim 9 and further comprising the step of reacting the first predetermined quantity of the dialdehyde solution with a predetermined quantity of a first reagent reactable with dialdehyde to cause a color change.

11. A method according to claim 10 wherein the reagent comprises a triazole.

12. A method according to claim 11 wherein the triazole comprises 4-amino-3-hydrazino-5-mercapto-1,2,4-triazole.

13. A method according to claim 9 and further comprising the following steps:
- (e) placing an optically transparent second vacuum ampoule into the handheld metering device;
- (f) aspirating a second predetermined quantity of the dialdehyde solution into the second vacuum ampoule;
- (g) passing light through the dialdehyde solution in the second vacuum ampoule onto a second sensor in the handheld metering device which is electrically connected to the microprocessor; and
- (h) via the microprocessor determining a concentration of a carboxylate in the dialdehyde solution based upon an output of the second sensor.

14. A method according to claim 13 and further comprising the step of reacting the second predetermined quantity of the dialdehyde solution with a second predetermined quantity of a second reagent reactable with carboxylate to cause a color change.

15. A method according to claim 14 wherein the second reagent comprises an acid and the second vacuum ampoule also contains a pH indicator.

16. A method according to claim 13 and further comprising the step of displaying results of steps (d) and (h) on the handheld device.

* * * * *